(12) United States Patent
Tanner

(10) Patent No.: US 9,409,852 B2
(45) Date of Patent: Aug. 9, 2016

(54) BIS(ARYLOXYALKYL) ESTERS OF AROMATIC POLYCARBOXYLIC ACIDS AND METHOD OF PREPARATION

(71) Applicant: James T Tanner, Greer, SC (US)

(72) Inventor: James T Tanner, Greer, SC (US)

(73) Assignee: ETHOX CHEMICALS, LLC, Greenville, SC (US)

( * ) Notice: Subject to any disclaimer, the term of this patent is extended or adjusted under 35 U.S.C. 154(b) by 0 days.

(21) Appl. No.: 14/040,562

(22) Filed: Sep. 27, 2013

(65) Prior Publication Data

US 2014/0031578 A1    Jan. 30, 2014

Related U.S. Application Data

(63) Continuation of application No. 13/067,571, filed on Jun. 9, 2011.

(60) Provisional application No. 61/344,861, filed on Oct. 26, 2010.

(51) Int. Cl.
| | | |
|---|---|---|
| *C07C 67/08* | (2006.01) | |
| *C07C 69/76* | (2006.01) | |
| *C07C 69/80* | (2006.01) | |
| *C07C 69/82* | (2006.01) | |
| *C08K 5/12* | (2006.01) | |
| *C07C 67/29* | (2006.01) | |

(52) U.S. Cl.
CPC .................. *C07C 67/08* (2013.01); *C07C 67/29* (2013.01); *C07C 69/76* (2013.01); *C07C 69/80* (2013.01); *C07C 69/82* (2013.01); *C08K 5/12* (2013.01); *C08K 2201/008* (2013.01); *Y10T 428/1379* (2015.01)

(58) Field of Classification Search
CPC ........ C07C 67/08; C07C 67/29; C07C 69/76; C07C 69/80; C07C 69/82; C08K 5/12
See application file for complete search history.

(56) References Cited

U.S. PATENT DOCUMENTS

| | | | | | |
|---|---|---|---|---|---|
| 2,906,737 | A | * | 9/1959 | York, Jr. | .................. C07C 67/08 528/279 |
| 3,071,604 | A | * | 1/1963 | Mohan | ...................... C11C 3/00 554/170 |
| 3,300,440 | A | * | 1/1967 | Prevorsek | ...................... 524/137 |
| 3,557,167 | A | * | 1/1971 | Hulsmann et al. | ............ 554/148 |
| 4,482,733 | A | * | 11/1984 | Ranade | ........................... 560/86 |

FOREIGN PATENT DOCUMENTS

| | | | | |
|---|---|---|---|---|
| JP | S54132502 | * | 10/1979 | |
| JP | H08302302 | * | 11/1996 | ............... C08K 5/10 |
| WO | WO2012/134643 | * | 10/2012 | ............... C08K 5/12 |

OTHER PUBLICATIONS

English Translation of JPH08302302, Nov. 19, 1996, pp. 1-10.*
English translation of Abstract of JPS54132502, dated Oct. 1979, pp. 1.*

* cited by examiner

*Primary Examiner* — Paul A Zucker
*Assistant Examiner* — Mark Luderer
(74) *Attorney, Agent, or Firm* — Isaac Angres

(57) ABSTRACT

The invention provides a compound of the formula:

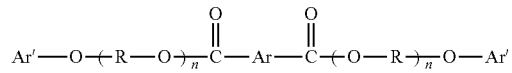

wherein Ar is selected from the group consisting of aryl, monosubstituted aryl and polysubstituted aryl, heteroaryl, monosubstituted heteroaryl and polysubstituted heteroaryl; Ar' is selected from the group consisting of aryl, monosubstituted aryl and polysubstituted aryl, heteroaryl, monosubstituted heteroaryl and polysubstituted heteroaryl; R is an alkylene radical having 2-20 carbon atoms; and n=1-20. The compounds of the invention are used with polymer resins to enhance their gas barrier properties.

2 Claims, 1 Drawing Sheet

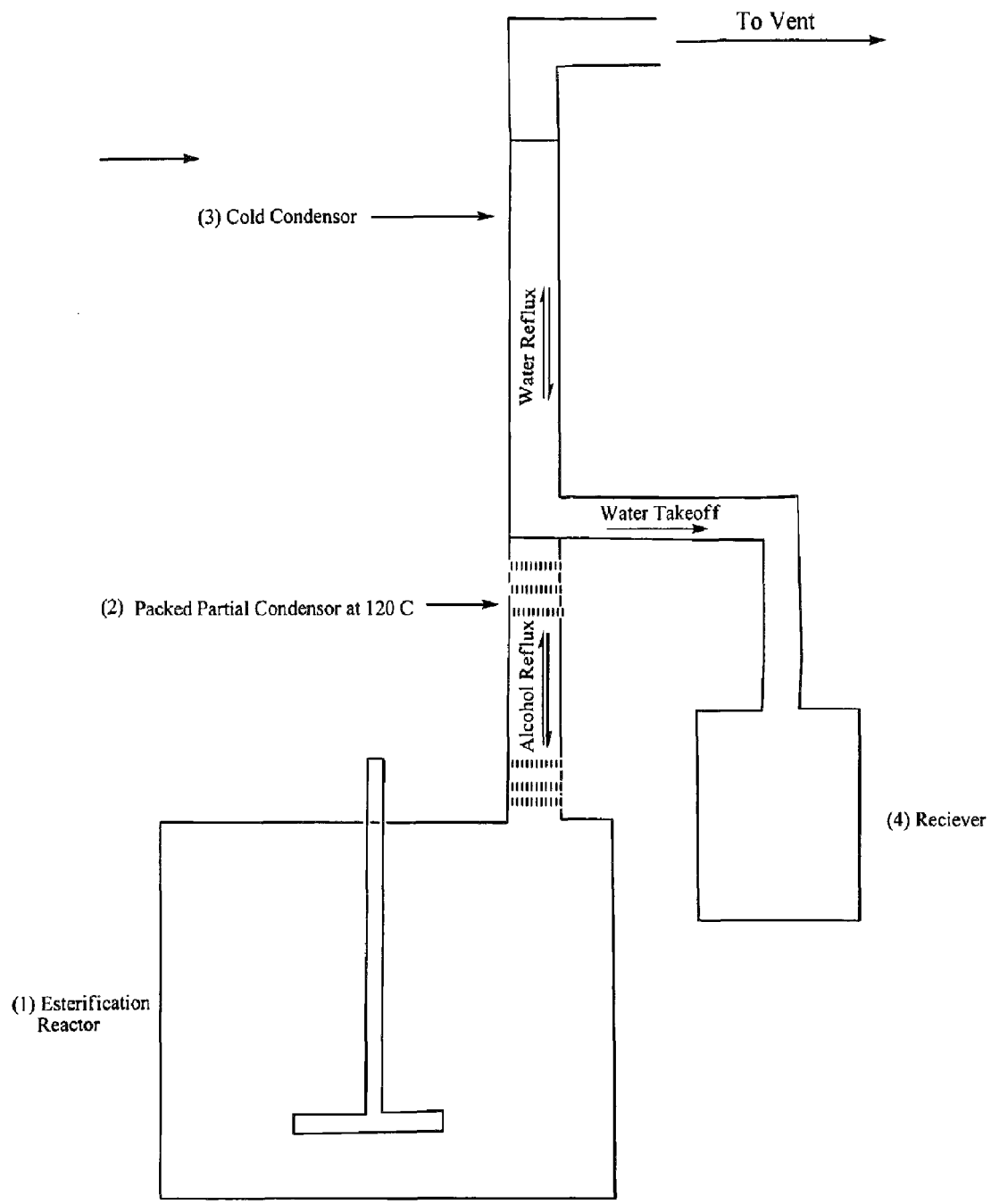

BIS(ARYLOXYALKYL) ESTERS OF AROMATIC POLYCARBOXYLIC ACIDS AND METHOD OF PREPARATION

This application is a continuation of U.S. pending application Ser. No. 13/067,571 filed Jun. 9, 2011. This application claims the priority benefit under 35 U.S.C. section 119 of U.S. provisional application Ser. No. 61/344,861 entitled "Novel Compositions and Method of Preparation" filed Oct. 26, 2010, which is in its entirety herein incorporated by reference.

FIELD OF INVENTION

This invention relates to new and useful additives for enhancing the gas barrier properties of polymeric resins and more in particular polyester resins. The invention is also directed to a polymer composition and method for reducing the permeability of gases through molded polymeric containers and films by incorporating into the polymer from which the container or film is formed an effective amount of a barrier-enhancing additive.

The invention further relates to a method for reducing gas permeability of shaped thermoplastic polymeric articles wherein the polymer from which the article is formed is selected from the group consisting of polyesters, polycarbonates, polyetherimides and polyethersulfones by adding the novel additives of the invention.

The invention also provides improved polyethylene terephthalate resin formulations containing novel additives for improving resistance to gas permeability.

The present invention is also directed to a polymer composition and method for improving the gas barrier performance of polymeric containers and films, and particularly containers for food and beverages which are molded from thermoplastic polyester polymers.

The invention further relates to a polymer composition and method for reducing the permeability of gases through molded polymeric containers, sheets and films by incorporating into the polymer from which the container, sheet or film is formed an effective amount of a barrier-enhancing additive of the type described herein.

The present invention also relates to polyester resins useful for forming packages for protecting comestibles. More specifically, it relates to polyester resins for forming film and molding containers which have improved gas barrier properties.

The instant invention also relates to packages for protecting carbonated beverages and to the polyesters from which such packages are made. More specifically, it relates to films and molded containers which are formed from such polyesters.

The present invention further provides containers having improved resistance to gas permeability. More specifically, the present invention also relates to a packaged beverage, and more particularly to enhancing the carbon dioxide and oxygen barrier properties of a container for a packaged beverage, thereby increasing the shelf life of its contents, by incorporating an additive into polyethylene terephthalate (PET) and its copolyesters.

BACKGROUND OF THE INVENTION

Formation of vessels such as drawn polyester bottles is very popular at the present because they provide substantial weight advantage over glass bottles especially in shipping weight. These polyester vessels have excellent transparency and somewhat acceptable but not optimum gas-barrier properties, and they have been broadly used as vessels for liquid detergents, shampoos, cosmetics, and also for carbonated drinks such as beer, cola and soda pop and refreshing drinks such as fruit juices and mineral water.

The drawn polyester bottles exhibit permeability to oxygen, carbon dioxide gas and the like though the permeability is small, while the gas permeability of completely sealed vessels such as glass bottles and metal cans is substantially zero. Accordingly, drawn polyester bottles are inferior to cans and glass bottles especially in the case of carbonated drinks, where loss of carbon dioxide gas occurs and there is a definite limit to the storage period.

Polyethylene terephthalate and its copolyesters (hereinafter referred to collectively as "PET") is the polyester of choice and is widely used to make containers for carbonated soft drinks, juice, water, and the like due to their excellent combination of clarity, mechanical, and somewhat acceptable gas barrier properties. In spite of these desirable characteristics, insufficient gas barrier of PET to oxygen and carbon dioxide limits the application of PET for smaller sized packages, as well as for packaging oxygen sensitive products, such as beer, juice, and tea products. A widely long felt need exists in the packaging industry to further improve the gas barrier properties of PET.

The relatively high permeability of PET to carbon dioxide limits the use of smaller PET containers for packaging carbonated soft drinks. The permeation rate of carbon dioxide through PET containers is in the range of 3 to 14 cc's per day or 1.5 to 2 percent per week loss rate at room temperature depending on the size of the container. A smaller container has a larger surface area to volume ratio resulting in a higher relative loss rate. For this reason, PET containers are currently used only as larger containers for packaging carbonated soft drinks, while metal cans and glass containers are the choice for smaller carbonated soft drink containers.

The amount of carbon dioxide that remains in a packaged carbonated soft drink determines its shelf life. Normally, carbonated soft drink containers are filled with approximately four volumes of carbon dioxide per volume of water. It is generally accepted in the industry that a packaged carbonated soft drink reaches the end of its shelf life when 17.5 percent of the carbon dioxide in the container is lost due to permeation of the carbon dioxide through the container side wall and closure. The permeability of PET to carbon dioxide therefore determines the shelf life of the packaged carbonated beverage and thus, the suitability of PET as a packaging material.

A wide variety of technologies have been developed or are being developed to enhance the barrier properties of PET to small gas molecules. For example, external or internal coatings for enhancing the gas barrier of PET containers have been developed. The coating layer is normally a very high barrier layer, either inorganic or organic, and slows down the diffusion of gases. Implementation of this technology, however, requires coating equipment not normally utilized in the manufacture of packaged beverages and therefore requires substantial capital investment, increased energy usage, and increased floor space. In many beverage packaging plants that are already crowded, the additional space is not an option.

Multi-layered containers have also been developed with a high barrier layer sandwiched between two or more PET layers. Implementation of this technology also requires substantial capital investment and delamination of the container layers impacts appearance, barrier, and mechanical performance of the containers.

A barrier additive for the PET or a polymer with inherent good barrier properties would be good solutions that are welcomed by the industry. Neither such solution requires additional capital investment, and therefore, does not have the limitations inherent with other technologies. A barrier additive can also be added during the injection molding process which gives more flexibility for downstream operations.

PET has been modified or blended with other components to enhance the gas barrier of the PET. Examples include polyethylene naphthalate (PEN)/PET copolymers or blends, isophthalate (IPA) modified PET, PET blended with polyethylene isophthalate (PEI) or a polyamide, such as nylon, and PET modified with resorcinol based diols. For a PET copolymer to achieve moderate barrier enhancement of 2× or higher, the modification is normally more than 10 to 20 weight or mole percent of the total co-monomers. When PET is modified to such a high level, the stretching characteristics of the PET are changed dramatically such that the normal PET container preform design could not be used in the manufacture of containers. Using these PET copolymers to mold conventional PET container preforms results in preforms that can not be fully stretched and the ultimate containers are very difficult, if not impossible, to make. Even if such a container can be made, it does not show improved barrier performance and shows deteriorated physical performance such that it can not be used to package carbonated soft drinks.

Furthermore, PET blends with polyamide such as nylon developed yellowness and haze and are not clear like conventional PET.

Accordingly, there is a long felt need in the art to enhance the barrier performance of PET for use in applications that will require enhanced barrier properties, such as in the packaging of carbonated beverages and oxygen sensitive beverages and foods, in a manner that does not cause substantial degradation of the PET, does not substantially impact the stretch ratio of the PET, and does not negatively impact the clarity of the PET.

Additionally, numerous examples of diesters of aromatic dicarboxylic acids have been disclosed in the prior art. For example, bis(hydroxyalkyl) esters of terephthalic and isophthalic acid are precursors for the preparation of poly(alkylene)arylates such as polyethylene terephthalate, polybutylene terphthalate, and polypropylene terephthalate. Simple diesters of phthalic acid or phthalic anhydride such as bis(2-ethylhexyl) phthalate are widely known as being effective plasticizers for a variety of plastics. Diesters of aromatic dicarboxylic acids such as dimethylterephthalate, diethylterephthalate and diphenylterephthalate have been demonstrated to be useful as barrier enhancing additives in aromatic polyesters such as polyethylene terephtahlate as disclosed in US patent application US 2006/0225568. Also, monoesters of hydroxybenzoic acid have also been disclosed that function as plasticizers in aromatic polyesters WO/01/12521.

OBJECTS OF THE INVENTION

It is a first object of the present invention to provide novel additives to improve the physical properties of polymeric formulations.

It is another object of the instant invention to provide novel additives to improve the physical properties of polyester resins.

A further object of the invention is to provide novel additives for copolyester resins.

A still further object of the invention is to provide novel additives to enhance the gas barrier properties of polymeric resins.

An additional object of the invention is to provide novel additives that when blended with polyester resins enhance the shelf life of carbonated beverages.

A still further object of the invention is to provide polymeric shaped products containing the novel additives of the invention.

An additional object of the present invention are gas barrier enhancing additives.

Still, another object of the invention are bis(aryloxylalkyl) esters of aromatic dicarboxylic acids.

A further object of the invention is to provide gas barrier enhancing additives base on bis(aryloxylalkyl) esters of aromatic dicarboxylic acids.

These and other objects of the present invention will more readily become apparent from the description and examples which follow.

SUMMARY OF THE INVENTION

The present invention and the inventive features described herein reside in the discovery of certain barrier-enhancing additives for thermoplastic polymers. The invention is barrier enhancing additives and a polymer composition that contains one or more of the additives and a method for reducing gas permeability of shaped polymeric articles produced from such a composition, such articles being generally selected from containers, sheets and films.

Polymeric articles, and particularly extruded film or injection stretch blow molded polyester (e.g., PET) bottles, which contain one or more of the barrier-enhancing additives described herein, exhibit substantially reduced oxygen and carbon dioxide permeability values when measured according to ASTM D3985 and water vapor permeability values when measured according to ASTM F1249 in comparison to corresponding polymeric articles which contained no barrier-enhancing additives.

The present invention provides a compound of the formula:

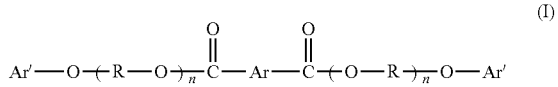

wherein Ar is selected from the group consisting of aryl, monosubstituted aryl and polysubstituted aryl, heteroaryl, monosubstituted heteroaryl and polysubstituted heteroaryl; Ar' is selected from the group consisting of aryl, monosubstituted aryl and polysubstituted aryl, heteroaryl, monosubstituted heteroaryl and polysubstituted heteroaryl; R is an alkylene radical having 2-20 carbon atoms; and n=1-20.

The present invention is also directed to a method for making a compound of the formula:

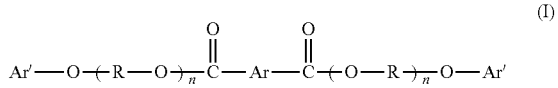

wherein Ar is selected from the group consisting of aryl, monosubstituted aryl and polysubstituted aryl, heteroaryl, monosubstituted heteroaryl and polysubstituted heteroaryl; Ar' is selected from the group consisting of aryl, monosubstituted aryl and polysubstituted aryl, heteroaryl, monosubstituted heteroaryl and polysubstituted heteroaryl; R is an alkylene radical having 2-20 carbon atoms; and n=1-20; which method comprises:

reacting a compound of the formula

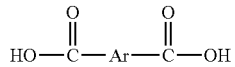

with a compound of the formula

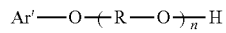

wherein Ar, Ar', R and n are as defined above, at a temperature range of about 150° C. to about 275° C. in the presence of a color stabilizer for a sufficient time until the diester is formed.

The invention further provides a polymer composition comprising: (a) a polymer selected from the group consisting of polyesters, polycarbonates, polyetherimides and polyethersulfones including their homopolymers, random or block copolymers and a blend or blends of such homopolymers and copolymers; and (b) a gas barrier additive in effective amounts to reduce gas permeability having the formula

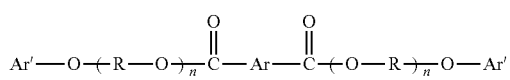

wherein Ar is selected from the group consisting of aryl, monosubstituted aryl and polysubstituted aryl, heteroaryl, monosubstituted heteroaryl and polysubstituted heteroaryl; Ar' is selected from the group consisting of aryl, monosubstituted aryl and polysubstituted aryl, heteroaryl, monosubstituted heteroaryl and polysubstituted heteroaryl; R is an alkylene radical having 2-20 carbon atoms; and n=1-20.

The present invention also provides a method for reducing gas permeability of shaped thermoplastic polymeric articles wherein the polymer from which the article is formed is selected from the group consisting of polyesters, polycarbonates, polyetherimides and polyethersulfones and wherein the method comprises the steps of: (1) incorporating into the polymer an amount of a barrier-enhancing additive or a mixture of barrier-enhancing additives effective to reduce gas permeability having the formula:

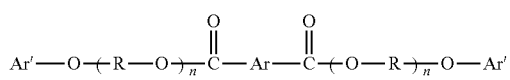

wherein Ar is selected from the group consisting of aryl, monosubstituted aryl and polysubstituted aryl, heteroaryl, monosubstituted heteroaryl and polysubstituted heteroaryl; Ar' is selected from the group consisting of aryl, monosubstituted aryl and polysubstituted 1aryl, heteroaryl, monosubstituted heteroaryl and polysubstituted heteroaryl; R is an alkylene radical having 2-20 carbon atoms; and n=1-20; and (2) shaping said polymeric articles.

The invention also provides a container comprising a polyester composition comprising a polyester and a gas barrier enhancing additive, wherein the gas barrier enhancing additive comprises a compound having the chemical structure of Formula II:

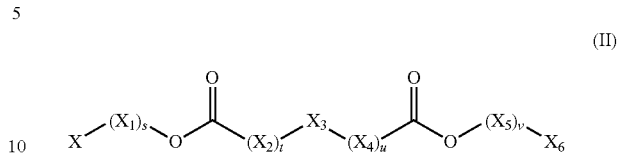

wherein X and $X_6$, independent of one another, comprise hydrogen, halide, heteroatom, hydroxyl, amino, amido, alkylamino, arylamino, alkoxy, aryloxy, nitro, acyl, cyano, sulfo, sulfato, mercapto, imino, sulfonyl, sulfenyl, sulfinyl, sulfamoyl, phosphonyl, phosphinyl, phosphoryl, phosphino, thioester, thioether, anhydride, oximno, hydrazino, carbamyl, phosphonic acid, phosphonato, or a $C_1$-$C_{10}$ monovalent hydrocarbon which is unsubstituted or substituted with one or more functional moieties; wherein $X_1$, $X_2$, $X_3$, $X_4$, and $X_5$, independent of one another, comprise a heteroatom or a $C_1$-$C_{10}$ divalent hydrocarbon, wherein each heteroatom or $C_1$-$C_{10}$ divalent hydrocarbon is unsubstituted or substituted with one or more functional moieties or one or more $C_1$-$C_{10}$ hydrocarbyls that are unsubstituted or substituted with one or more functional moieties; and wherein s, t, u, and v, independent of one another, is a number from 0 to 10; wherein when $X_3$ comprises a $C_6$ or $C_{10}$ divalent aromatic hydrocarbon, X and $X_6$, independent of one another, comprise a hydrogen, halide, heteroatom, hydroxyl, amino, amido, alkylamino, arylamino, alkoxy, aryloxy, nitro, acyl, cyano, sulfo, sulfato, mercapto, imino, sulfonyl, sulfenyl, sulfinyl, sulfamoyl, phosphonyl, phosphinyl, phosphoryl, phosphino, thioester, thioether, anhydride, oximno, hydrazino, carbamyl, phosphonic acid, phosphonato, or a $C_3$-$C_{10}$ monovalent cyclic or heterocyclic non-aryl hydrocarbon that are unsubstituted or substituted with one or more functional moieties.

The invention also provides a polyester composition comprising a polyester and a gas barrier additive, wherein the gas barrier enhancing additive comprises a compound having the chemical structure of Formula II:

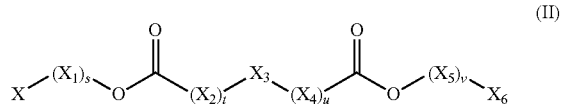

wherein X and $X_6$, independent of one another, comprise hydrogen, halide, heteroatom, hydroxyl, amino, amido, alkylamino, arylamino, alkoxy, aryloxy, nitro, acyl, cyano, sulfo, sulfato, mercapto, imino, sulfonyl, sulfenyl, sulfinyl, sulfamoyl, phosphonyl, phosphinyl, phosphoryl, phosphino, thioester, thioether, anhydride, oximno, hydrazino, carbamyl, phosphonic acid, phosphonato, or a $C_1$-$C_{10}$ monovalent hydrocarbon which is unsubstituted or substituted with one or more functional moieties; wherein $X_1$, $X_2$, $X_3$, $X_4$, and $X_5$, independent of one another, comprise a heteroatom or a $C_1$-$C_{10}$ divalent hydrocarbon, wherein each heteroatom or $C_1$-$C_{10}$ divalent hydrocarbon is unsubstituted or substituted with one or more functional moieties or one or more $C_1$-$C_{10}$ hydrocarbyls that are unsubstituted or substituted with one or more functional moieties; and wherein s, t, u, and v, independent of one another, is a number from 0 to 10; wherein when $X_3$ comprises a $C_6$ or $C_{10}$ divalent aromatic hydrocarbon, X and $X_6$, independent of one another, comprise a hydrogen, halide, heteroatom, hydroxyl, amino, amido, alkylamino, arylamino, alkoxy, aryloxy, nitro, acyl, cyano, sulfo, sulfato, mercapto, imino, sulfonyl, sulfenyl, sulfinyl, sulfamoyl, phosphonyl, phosphinyl, phosphoryl, phosphino, thioester, thioether, anhydride, oximno, hydrazino, carbamyl, phosphonic acid, phosphonato, or a $C_3$-$C_{10}$ monovalent cyclic or heterocyclic non-aryl hydrocarbon that are unsubstituted or substituted with one or more functional moieties.

The invention further provides a shaped thermoplastic polymeric article comprising a base polymer having physically incorporated therein an amount of one or more barrier-enhancing additives effective to reduce permeability of the shaped article to gases when compared to the shaped article not having the one or more barrier-enhancing additives incorporated therein, wherein the one or more barrier-enhancing additives are selected from the group consisting of compounds of the formula:

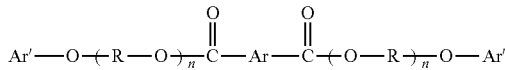

wherein Ar is selected from the group consisting of aryl, monosubstituted aryl and polysubstituted aryl, heteroaryl, monosubstituted heteroaryl and polysubstituted heteroaryl; Ar' is selected from the group consisting of aryl, monosubstituted aryl and polysubstituted aryl, heteroaryl, monosubstituted heteroaryl and polysubstituted heteroaryl; R is an alkylene radical having 2-20 carbon atoms; and n=1-20.

DESCRIPTION OF THE PREFERRED EMBODIMENTS

Applicant has found that the bis(aryloxylalkyl) esters of aromatic dicarboxylic acids such as terephthalic, isophthalic, and napthalenedicarboxylic acids are novel and new compositions of matter useful in barrier applications. Also, a simple and convenient process is disclosed for their preparation.

In one embodiment, our invention relates to compounds of the formula:

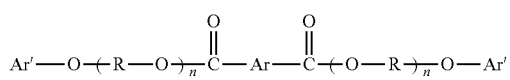

wherein Ar is selected from the group consisting of aryl, monosubstituted aryl and polysubstituted aryl, heteroaryl, monosubstituted heteroaryl and polysubstituted heteroaryl; Ar' is selected from the group consisting of aryl, monosubstituted aryl and polysubstituted aryl, heteroaryl, monosubstituted heteroaryl and polysubstituted heteroaryl; R is an alkylene radical having 2-20 carbon atoms; and n=1-20.

The aryl group in the compounds of formula (I) is selected from the group consisting of phenyl, naphthyl, biphenyl, terphenyl, and all positional isomeric derivatives thereof. The mono and polysubstituted aryl group of compounds of the formula (I) is selected from the group consisting of substituted phenyl, substituted naphthyl, substituted biphenyl, substituted terphenyl, and all positional isomeric derivatives thereof.

The substituent(s) in the aryl groups is selected from the group consisting of —O$^{(-)}$, —OH, —OR, —OC$_6$H$_5$, —OCOCH$_3$, —NH$_2$, —NR$_2$, —NHCOCH$_3$—R, —C$_6$H$_5$, —NO$_2$, —NR$_3^{(+)}$, —PR$_3^{(+)}$, —SR$_2^{(+)}$, —SO$_3$H, —SO$_2$R, —CO$_2$H, —CO$_2$R, —CONH$_2$, —CHO, —COR, —CN, —F, —Cl, —Br, —I, —CH$_2$Cl, and —CH=CHNO$_2$.

More specifically, the invention is directed to compounds of formula:

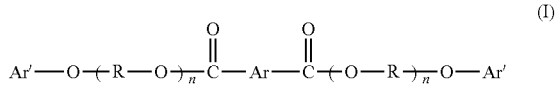

in which Ar is an arylene group such as terephthalyl, isophthalyl, naphthyl, and other aromatic moiety containing radicals, R is an alkylene radical such as ethylene, propylene, isopropylene and butylene, and n is an integer between 1 and about 20. Ar' is an arylene group or substituted arylene group such as terephthalyl, isophthalyl, naphthyl or other aromatic moiety containing radicals.

Compounds of formula (I) are derived from aromatic dicarboxylic acids and aryloxyalkanols or substituted aryloxyalkanols of formula (II) in which Ar' is an arylene group or substituted

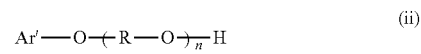

arylene group such as terepthalyl, isophthalyl, naphthyl and other aromatic polycarboxylic acids and R is an alkylene radical such as ethylene, propylene, isopropylene, butylenes, and C5-C18 alkylene and n is an integer from about 1 to about 20. Suitable compounds of formula (II) that are useful in the preparation of compounds of formula (I) include, but are not limited to alkoxylated phenol, alkoxylated napthols, alkoxylated hydroxy biphenyls, and biphenyl ethers, alkoxylated styrenated phenols as well as their substituted derivatives.

Particular examples of compounds of formula (I) include the condensation product of terephthalic acid and 2-phenoxyethanol (iii);

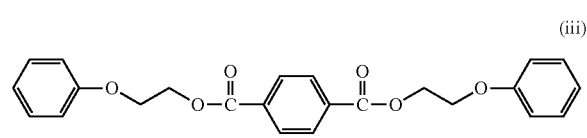

the condensation product of terephthalic acid and ethoxylated 2-naphthol (iv);

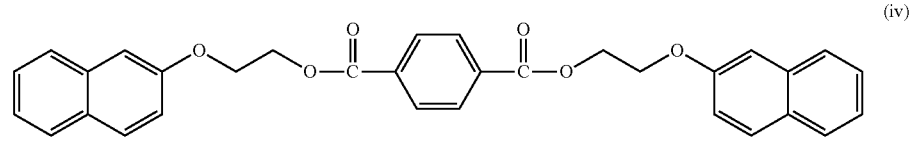 [SMILES: O=C(OCCOc1ccc2ccccc2c1)c1ccc(C(=O)OCCOc2ccc3ccccc3c2)cc1]

the condensation product of terephthalic acid and ethoxylated 1-naphthol (v), and the analogous

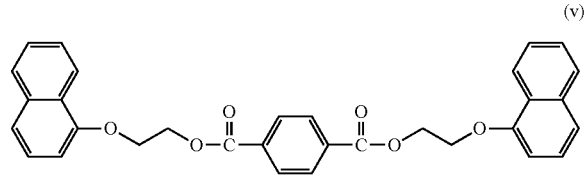 [SMILES: O=C(OCCOc1cccc2ccccc12)c1ccc(C(=O)OCCOc2cccc3ccccc23)cc1]

(v)

and isophthalic and naphthalenedicarboxylic acid derivatives of the foregoing alcohols.

Regarding the method of preparation of the novel barrier additives of the invention, it is well known in the art that the synthesis of esters of aromatic mono and dicarboxylic acids often requires that the alcohol or glycol component be used in substantial excess. This is due to the low solubility and high melting points of aromatic dicarboxylic acids such as terephthalic and isophthalic acids. The glycol or alcohol component is used in excess in order to aid in the solubilization of the acid component, and also in order to drive the equilibrium esterification reaction to the desired ester. Esterification catalysts are also often necessary in order to achieve an acceptable reaction rate. In certain applications where aromatic esters have been used as additives, such as food packaging and cosmetics, it is desirable for the additive to be of high purity. It is therefore desirable to employ a process of preparation in which additional components such as catalysts can be minimized and in which the desired esters can be produced in high yield and in high purity.

The process of preparing the novel barrier additives of the invention allows the synthesis of the compositions of formula (I) in high purity and yield without the use of a large excess of the alcohol or glycol ether component, and without the use of conventional esterification catalysts that would have to be neutralized and filtered or somehow removed from the reaction product. The reaction apparatus employed in the synthesis of compositions of the present invention is represented schematically by FIG. 1. The apparatus consists of a conventional esterification reactor that has been modified with a heated packed partial condenser. The temperature of the partial condenser is maintained above the boiling point of water and below the boiling of the alcohol or glycol ether reaction component thus allowing continuous reflux of the alcohol or glycol ether component while simultaneously removing the water of esterification. The advantages of this method are: (1) Loss of alcohol or glycol ether in the water distillate is prevented making the use of a large excess of this component unnecessary, (2) The water of esterification is not contaminated with the alcohol or glycol ether component negating a costly and time consuming separation. (3) The final time required to vacuum strip the excess alcohol or glycol ether component from the reaction mixture is greatly reduced. (4) The method yields esters in high purity that are suitable as additives in food contact and cosmetic applications.

In a further embodiment, the present invention resides in the discovery that oxygen, water vapor and carbon dioxide (CO2) permeability values for shaped polymeric containers and films can be substantially reduced by incorporating into the base polymer from which the articles are formed effective amounts of a barrier-enhancing additive of the type defined herein.

Suitable polyesters that can be compounded with the additives of the invention are produced from the reaction of a diacid or diester component comprising at least 65 mole % terephthalic acid or $C_1$-$C_4$ dialkyl terephthalate, preferably at least 70 mole %, more preferably at least 75 mole %, even more preferable at least 95 mole %, and a glycol/diol component comprising at least 65 mole % diol, preferably at least 70 mole %, more preferably 75 mole %, even more preferably at least 95 mole %. It is also preferable that the diacid component is terephthalic acid and the diol component is ethylene glycol. The mole percentage for all of the diacid component totals 100 mole %, and the mole percentage for all of the diol component totals 100 mole %.

Where the polyester components are modified by one or more diol components other than ethylene glycol, suitable diol components of the described polyesters may be selected from the diols listed else where herein, which diols include, for example, 1,2-propanediol; 1,3-propanediol; 1,4-butanediol; 2,2-dimethyl-1,3-propanediol; 1,6-hexane-diol; 1,2-cyclohexane-diol; 1,4-cyclohexanediol; 1,2-cyclohexanedimethanol; 1,3-cyclo-hexanedimethanol; and diols containing one or more oxygen atoms in the chain, for example, diethylene glycol, triethylene glycol, dipropylene glycol and similar glycols, and mixtures of all of the foregoing. In general, the diols contain 2-18, preferably 2 to 8, carbon atoms. Cycloaliphatic diols can be employed in their cis- or trans-forms, of as mixtures of both forms. Preferred modifying diol components are 1,4-cyclohexane-dimethanol or diethylene glycol, or mixtures of thereof.

Where the polyester components are modified by one or more acid components other than terephthalic acid, the suitable acid components (aliphatic, alicyclic or aromatic dicarboxylic acids) of the linear polyester may be, for example, isophthalic acid, 1,4-cyclohexanedicarboxylic acid, 1,3-cyclohexanedicarboxylic acid, succinic acid, glutaric acid, adipic acid, sebacic acid, 1,12-dodecanedioic acid, 2,6-napthalenedicarboxylic acid, bibenzoic acid, and similar diacids, or mixtures thereof. In polymer preparation it is often preferred to use a functional derivative of the diacid, for example, the dimethyl, diethyl, dipropyl and similar diester of the dicarboxylic acid. The anhydrides and acid halides of these diacids may also be used where practical.

Also, another contemplated polyester resin is a modified polyester made by reacting at least 85 mole % terephthalate from either terephthalic acid or dimethyl terephthalate with any of the above co-monomers.

The polyesters of the present invention can be produced by any of the conventional methods of producing polyethylene terephthalate. Conventional methods of producing polyethylene terephthalate are well known and comprise reacting terephthalic acid with ethylene glycol at a temperature of about 200° C. to about 250° C. forming monomer and water. Because the reaction is reversible, the water is continuously removed, driving the reaction to the production of monomer. Next, the monomer undergoes a polycondensation reaction to form the polymer. During the reaction of the terephthalic acid and ethylene glycol it is not necessary to have catalyst present. Generally, during the polycondensation reaction, a catalyst is preferably present, for example, an antimony catalyst or other catalyst known in the art. When diester are used in preparation of the polymer, other diacids and other diols may conventionally employed various catalysts as is well known in the art.

The polyester composition of the invention typically has an I.V. from about 0.65 dL/g to about 1.0 dL/g.

Particularly useful polyester resins are the polyester resins sold by Invista (Spartanburg, S.C.). A resin designated as 1103 A is particularly useful. Other resins that can be used include those listed in Table 1.

TABLE 1

| Product | Type | Luster | IV |
|---|---|---|---|
| OxyClear ® Barrier Resin | Copolymer | Clear | 0.84 |
| Polyclear ® PET 1101 | Copolymer | Clear | 0.83 |
| Polyclear ® PET 3300 | Copolymer | Clear | 0.72 |
| Polyclear ® EBM PET | Copolymer | Clear | 1 |
| Polyclear ® PET T94N | Copolymer | Clear | 0.87 |
| PolyShield ® Resin | Copolymer | Clear | 0.84 |

In accordance with a further preferred embodiment of the present invention, there is provided polymer compositions containing the gas barrier additive in an amount in the range of about 0.05 to about 12 weight percent of the polyester composition.

In a most preferred embodiment there is provided polyester compositions wherein the gas barrier additive is present in the polyester composition in an amount in the range of about 0.05 to about 12 weight percent of the polyester composition.

The compositions of the invention are prepared by forming a uniform physical blend, or mixture, comprising the base polymer and one or more barrier-enhancing additives in the desired concentrations. As used herein with reference to the invention, the term "composition" is intended to mean a physical blend or mixture. Water-sensitive base polymers, such as, for example, polyesters should preferably be thoroughly dried by heating under air or nitrogen flow or vacuum as known to those experienced in the art. The mixture is then heated and extruded or molded at a sufficiently high temperature to melt the base polymer and provide for sufficient mixing of the additive or mixture of additives within the base polymer matrix. By way of example using PET, such melt temperature ranges from about 255° C. to 300° C. The composition thus produced comprises the barrier-enhancing additive (or mixture of such additives) substantially in its (their) original molecular form; that is, only small amounts of barrier-enhancing additive have been observed to react with the base polymer via trans-esterification or other reaction mechanism typical of the functional groups present. It is preferred to prepare and extrude or mold the polymer composition under conditions of relatively low temperature and processing residence time which thereby minimizes the opportunity for the barrier-enhancing additives to react with the base polymer. Best performance in terms of desirable mechanical properties of polymeric containers and films produced according to the invention is achieved when no more than about 10% of the gas barrier-enhancing additive has reacted with the base polymer. As a consequence of any reaction of a gas barrier-enhancing additive within the scope of the invention with a base polymer, the molecular weight of the starting base polymer may decrease.

In a further embodiment of the invention, the gas barrier enhancing additives of the invention may be blended with other physical property improving additives known in the art i.e., mechanical properties improving additives such as creep control agents, impact strength additives, flow control additives, melt flow control additives and the like.

In a further embodiment the invention also provides a container comprising a polyester composition comprising a polyester; a mechanical property improving agent; and a gas barrier enhancing additive comprises a compound having the chemical structure of Formula II:

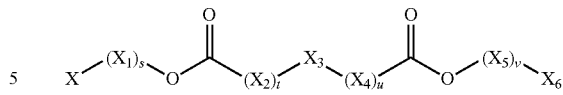

(II)

wherein X and $X_6$, independent of one another, comprise hydrogen, halide, heteroatom, hydroxyl, amino, amido, alkylamino, arylamino, alkoxy, aryloxy, nitro, acyl, cyano, sulfo, sulfato, mercapto, imino, sulfonyl, sulfenyl, sulfonyl, sulfamoyl, phosphonyl, phosphinyl, phosphoryl, phosphino, thioester, thioether, anhydride, oximino, hydrazino, carbamyl, phosphonic acid, phosphonato, or a $C_1$-$C_{10}$ monovalent hydrocarbon which is unsubstituted or substituted with one or more functional moieties; wherein $X_1$, $X_2$, $X_3$, $X_4$, and $X_5$, independent of one another, comprise a heteroatom or a $C_1$-$C_{10}$ divalent hydrocarbon, wherein each heteroatom or $C_1$-$C_{10}$ divalent hydrocarbon is unsubstituted or substituted with one or more functional moieties or one or more $C_1$-$C_{10}$ hydrocarbyls that are unsubstituted or substituted with one or more functional moieties; and wherein s, t, u, and v, independent of one another, is a number from 0 to 10; wherein when $X_3$ comprises a $C_6$ or $C_{10}$ divalent aromatic hydrocarbon, X and $X_6$, independent of one another, comprise a hydrogen, halide, heteroatom, hydroxyl, amino, amido, alkylamino, arylamino, alkoxy, aryloxy, nitro, acyl, cyano, sulfo, sulfato, mercapto, imino, sulfonyl, sulfenyl, sulfinyl, sulfamoyl, phosphonyl, phosphinyl, phosphoryl, phosphino, thioester, thioether, anhydride, oximno, hydrazino, carbamyl, phosphonic acid, phosphonato, or a $C_3$-$C_{10}$ monovalent cyclic or heterocyclic non-aryl hydrocarbon that are unsubstituted or substituted with one or more functional moieties.

EXAMPLES

The present invention is illustrated by the following Examples, but should not be construed to be limited thereto. In the Examples, each reactant is specified in grams and moles unless specified otherwise.

Example 1

Condensation Product of Terephthalic Acid and 2-Phenoxyethanol 398.0 grams of purified terephthalic acid (2.4 moles) and 732.0 grams of 2-phenoxyethanol (5.3 moles) were charged to a 2 liter round bottom flask equipped with a mechanical stirrer, inert gas inlet, and thermocouple. A packed partial condenser, wrapped with heat tape was placed between the cold condenser and water trap. The packed partial condenser was then heated to 120° C., 0.1 wt. % of hypophosphorous acid was added as a color stabilizer and the reaction mixture was heated to 245-250° C. at which time the 2-phenoxyethanol began refluxing. The slurry of terephthalic acid and 2-phenoxyethanol was maintained between 245-250° C. for 24 hr at which time the reaction mixture was clear. GC analysis of the reaction mixture showed 99.4% diester and 0.6% monoester. The excess 2-phenoxyethanol was then stripped under vacuum until none was detected by GC analysis. The reaction mixture was cooled to 120° C. and then decanted to yield 1015.0 g of diester as a white solid.

Example 2

Condensation Product of Isophthalic Acid and 2-Phenoxyethanol 398.0 grams of purified isophthalic acid (2.4 moles) and 732.0 grams of 2-phenoxyethanol (5.3 moles) were charged to a 2 liter round bottom flask equipped with a mechanical stirrer, inert gas inlet, and thermocouple. A packed partial condenser, wrapped with heat tape was placed between the cold condenser and water trap. The packed partial condenser was then heated to 120° C., 0.1 wt. % of hypophosphorous acid was added as a color stabilizer, and the reaction mixture was heated to 245-250° C. at which time the 2-phenoxyethanol began refluxing. The slurry of terephthalic acid and 2-phenoxyethanol was maintained between 245-250° for 24 hr at which time the reaction mixture was clear. GC analysis of the reaction mixture showed 99.4% diester and 0.6% monoester. The excess 2-phenoxyethanol was then stripped under vacuum until none was detected by GC analysis. The reaction mixture was cooled to 120° C. and then decanted to yield 1010.0 g of diester as a white solid.

Example 3

Condensation Product of 2,6-Naphthalene Dicarboxylic Acid with 2-Phenoxyethanol 519.0 grams of 2,6-naphthalenedicarboxylic acid (2.4 moles) and 732.0 grams of 2-phenoxyethanol (5.3 moles) were charged to a 2 liter round bottom flask equipped with a mechanical stirrer, inert gas inlet, and thermocouple. A packed partial condenser, wrapped with heat tape was placed between the cold condenser and water trap. The packed partial condenser was then heated to 120° C., 0.1 wt. % of hypophosphorous acid was added as a color stabilizer, and the reaction mixture was heated to 245-250° C. at which time the 2-phenoxyethanol began refluxing. The slurry of terephthalic acid and 2-phenoxyethanol was maintained between 245-250° C. for 24 hr at which time the reaction mixture was clear. GC analysis of the reaction mixture showed 99.4% diester and 0.6% monoester. The excess 2-phenoxyethanol was then stripped under vacuum until none was detected by GC analysis. The reaction mixture was cooled to 120° C. and then decanted to yield 1150.0 g of diester as a white solid.

Example 4

Condensation Product of Terephthalic Acid and 2-Phenoxyethanol 1,592.0 grams of purified terephthalic acid (9.6 moles) and 2,928.0 grams of 2-phenoxyethanol (21.2 moles) were charged to a 10 liter round bottom flask equipped with a mechanical stirrer, inert gas inlet, and thermocouple. A packed partial condenser, wrapped with heat tape was placed between the cold condenser and water trap. The packed partial condenser was then heated to 120° C., 0.4 wt. % of hypophosphorous acid was added as a color stabilizer and the reaction mixture was heated to 245-250° C. at which time the 2-phenoxyethanol began refluxing. The slurry of terephthalic acid and 2-phenoxyethanol was maintained between 245-250° C. for 24 hr at which time the reaction mixture was clear. GC analysis of the reaction mixture showed 99.4% diester and 0.6% monoester. The excess 2-phenoxyethanol was then stripped under vacuum until none was detected by GC analysis. The reaction mixture was cooled to 120° C. and then decanted to yield 4,060.0 g of diester as a white solid.

Example 5

Condensation Product of Phthalic Acid and 2-Phenoxyethanol 398.0 grams of purified phthalic acid (2.4 moles) and 732.0 grams of 2-phenoxyethanol (5.3 moles) were charged to a 2 liter round bottom flask equipped with a mechanical stirrer, inert gas inlet, and thermocouple. A packed partial condenser, wrapped with heat tape was placed between the cold condenser and water trap. The packed partial condenser was then heated to 120° C., 0.1 wt. % of hypophosphorous acid was added as a color stabilizer, and the reaction mixture was heated to 245-250° C. at which time the 2-phenoxyethanol began refluxing. The slurry of terephthalic acid and 2-phenoxyethanol was maintained between 245-250° for 24 hr at which time the reaction mixture was clear. GC analysis of the reaction mixture showed 99.4% diester and 0.6% monoester. The excess 2-phenoxyethanol was then stripped under vacuum until none was detected by GC analysis. The reaction mixture was cooled to 120° C. and then decanted to yield 1010.0 g of diester as a white solid.

Example 6

Condensation Product of Terephthalic Acid and 2-Phenoxyethanol 796.0 grams of purified terephthalic acid (4.8 moles) and 1,464.0 grams of 2-phenoxyethanol (10.6 moles) were charged to a 5 liter round bottom flask equipped with a mechanical stirrer, inert gas inlet, and thermocouple. A packed partial condenser, wrapped with heat tape was placed between the cold condenser and water trap. The packed partial condenser was then heated to 120° C., 0.2 wt. % of hypophosphorous acid was added as a color stabilizer and the reaction mixture was heated to 245-250° C. at which time the 2-phenoxyethanol began refluxing. The slurry of terephthalic acid and 2-phenoxyethanol was maintained between 245-250° C. for 24 hr at which time the reaction mixture was clear. GC analysis of the reaction mixture showed 99.4% diester and 0.6% monoester. The excess 2-phenoxyethanol was then stripped under vacuum until none was detected by GC analysis. The reaction mixture was cooled to 120° C. and then decanted to yield 2,030.0 g of diester as a white solid.

Example 7

A polyester composition was prepared by blending a ground 1103 A polyester resin (Invista, Spartanburg, S.C.) with either 3, 4 or 5 wt % of PEM, a gas barrier additive having the chemical formula:

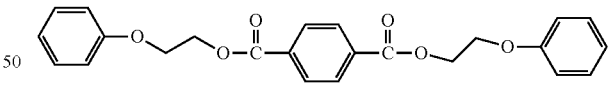

The polyester composition was injection molded using conventional methods to obtain a container preform. The container preforms appeared to be of good quality in terms of clarity and shape without any indication of buildup on the core pin or in the thread splits and other parts of the injection molder, indicating there was no substantial plate-out on the injection molding equipment. The container preforms then were stretch blow molded using conventional methods to obtain bottles which were clear, colorless to the eye, and indistinguishable from one another.

Although the present invention has been described with reference to specific details of certain embodiments thereof, it is not intended that such detail should be regarded as limitations upon the scope of the invention, except as and to the extent that they are included in the accompanying claims.

What is claimed is:

1. A method for making a compound of the formula:

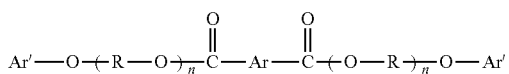

wherein Ar is selected from the group consisting of aryl, monosubstituted aryl and polysubstituted aryl, heteroaryl, monosubstituted heteroaryl and polysubstituted heteroaryl; Ar' is selected from the group consisting of aryl, monosubstituted aryl and polysubstituted aryl, heteroaryl, monosubstituted heteroaryl and polysubstituted heteroaryl; R is an alkylene radical having 2-20 carbon atoms; and n=1-20; which method comprises:

reacting in a esterification reactor having a heated packed partial condenser a compound of the formula

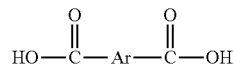

with a compound of the formula

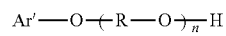

wherein Ar, Ar', R and n are as defined above, at a temperature range of about 150° C. to about 275° C. in the presence 0.1 wt. % of hypophosphorous acid as of a color stabilizer for a sufficient time until the diester is formed and wherein the temperature of the packed partial condenser is maintained above the boiling point of water and below the boiling of the alcohol or glycol ether reaction component thus allowing continuous reflux of the alcohol or glycol ether component while simultaneously removing the water of esterification and wherein said method provides a product mixture containing 99.4% diester and 0.6% monoester.

2. The method of claim 1, wherein the temperature of the partial condenser is maintained in the range of about 115° C. to about 135° C.

* * * * *